(12) United States Patent
Gaines et al.

(10) Patent No.: US 7,712,642 B2
(45) Date of Patent: May 11, 2010

(54) GLOVE DONNING AND REMOVAL APPARATUS

(76) Inventors: Ronald J. Gaines, 5807 Rushwood Dr., Dublin, OH (US) 43017; Lynne H. Gaines, 5807 Rushwood Dr., Dublin, OH (US) 43017; Shelly H. Schaefer, 114 E. Harrison St., Maumee, OH (US) 43537

( * ) Notice: Subject to any disclaimer, the term of this patent is extended or adjusted under 35 U.S.C. 154(b) by 1148 days.

(21) Appl. No.: 11/336,033

(22) Filed: Jan. 20, 2006

(65) Prior Publication Data

US 2007/0170213 A1  Jul. 26, 2007

(51) Int. Cl.
*A47G 25/80* (2006.01)
(52) U.S. Cl. ..................... 223/111
(58) Field of Classification Search ......... 223/111–120, 223/1, DIG. 1; 221/70–73
See application file for complete search history.

(56) References Cited

U.S. PATENT DOCUMENTS

| | | | | |
|---|---|---|---|---|
| 4,371,987 A | * | 2/1983 | Brasfield | ........................ 2/162 |
| 4,773,532 A | * | 9/1988 | Stephenson | .................. 206/278 |
| 4,909,413 A | * | 3/1990 | McCutcheon | ................... 221/1 |
| 6,003,722 A | * | 12/1999 | Thurner | ........................ 221/25 |
| 6,375,034 B1 | * | 4/2002 | Corbett | ........................ 221/46 |
| 6,706,243 B1 | * | 3/2004 | Sias et al. | ...................... 422/28 |
| 6,953,130 B2 | * | 10/2005 | Corbett | ........................ 221/191 |
| 2005/0155133 A1 | * | 7/2005 | Sato | ............................... 2/159 |

* cited by examiner

*Primary Examiner*—Shaun R Hurley
*Assistant Examiner*—Andrew W Sutton
(74) *Attorney, Agent, or Firm*—Thomas S. Baker, Jr.

(57) ABSTRACT

A glove donning and removal apparatus for donning, a glove sandwiched between a pair of upper and lower feed sheets is advanced towards a glove dispensing opening. Grabber arms expand the glove hand opening to enable a user to easily insert a hand into the hand opening. For removal, secondary top and bottom feed rolls having adhesively coated top and bottom feed sheets are moved towards a glove removal opening. The adhesive-coated top and bottom feed sheets cooperate to strip a glove from a user's hand when the hand is placed on a glove removal surface in the glove removal opening.

26 Claims, 15 Drawing Sheets

GLOVE DONNING AND REMOVAL APPARATUS

CROSS-REFERENCES

None.

BACKGROUND OF THE INVENTION

The present invention relates to a glove donning and removal apparatus.

Disposable gloves have been utilized in the health care industry, food handling industry and elsewhere for many years. In many instances, disposable gloves are preferred over the current standard practice of washing hands for at least two minutes with an appropriate disinfectant which can ultimately compromise skin integrity and lead to skin infection and/or abrasion. In health care, the use of gloves by a heath care provider protects a patient from any contaminants that may reside on the health care provider. Of course, they also protect the heath care provider from possible contamination resulting from handling a patient.

While disposable gloves are preferred and utilized by most health care providers, special precautions must be taken to insure that the gloves are not contaminated by the user as they are being donned and that other stored gloves are not contaminated or touched by the user. Additionally, precautions must be taken during the glove removal process to ensure that the hands of a user do not contact the outer surface of the glove and become exposed to any contamination thereon and that removal of the glove does not splatter or aerosolize contaminated matter. Lastly, used disposable gloves must be disposed of safely.

It is desirable to provide a glove donning and removal apparatus that maintains the cleanliness of the gloves until they are utilized, assists a user in donning and removing a glove, prevents contamination of a glove during the donning process, prevents a user's hand from contacting the outer or working surface of a glove during the removal process, and immediately encases or seals a used glove for disposal after the glove has been removed.

SUMMARY OF THE INVENTION

A glove donning and removal apparatus has a housing with a glove dispensing opening and a glove removal opening, a primary feed roll having a spaced pair of upper and lower feed sheets at least partially received within the housing, and a glove having a cuff defining a hand opening sandwiched between the upper and lower feed sheets. A feed sheet drive advances the upper and lower feed sheets and the glove toward the glove dispensing opening. A pair of grabbers, each having a base and an arm affixed to the base, are positioned one on each side of the feed roll. A grabber drive connected to the grabbers moves the grabber arms into engagement with the glove cuff, moves the grabber arms apart to cause the glove hand opening to expand, and rotates to secure the glove to enable the user to easily insert a hand into the glove opening. Thereafter, the grabber drive rotates in the opposite direction to release the glove after the user's hand has been inserted into the glove.

A glove removal surface resides adjacent the glove removal opening. A secondary top feed roll having a top feed sheet and a secondary bottom feed roll having a bottom feed sheet are at least partially received in the glove removal opening. An adhesive coating is formed on one side of at least one of the top and bottom feed sheets. Guides cause the bottom feed sheet to pass over the glove removal surface. Guides also cause the top feed sheet to pass above the glove removal surface. Lastly, guides cause the top and bottom feed sheets to converge in the glove removal opening such that the top and bottom feed sheets cooperate to strip a glove from a user's hand when the gloved hand is placed on the glove removal surface in the glove removal opening such that it rests upon the bottom feed sheet. The glove is encased between the top and bottom feed sheets subsequent to being removed from the hand of the user. A storage roll drive for a storage roll winds the top and bottom feed sheets containing the encased gloves onto the storage roll after they have passed through the glove removal opening.

DETAILED DESCRIPTION

Figure 1:
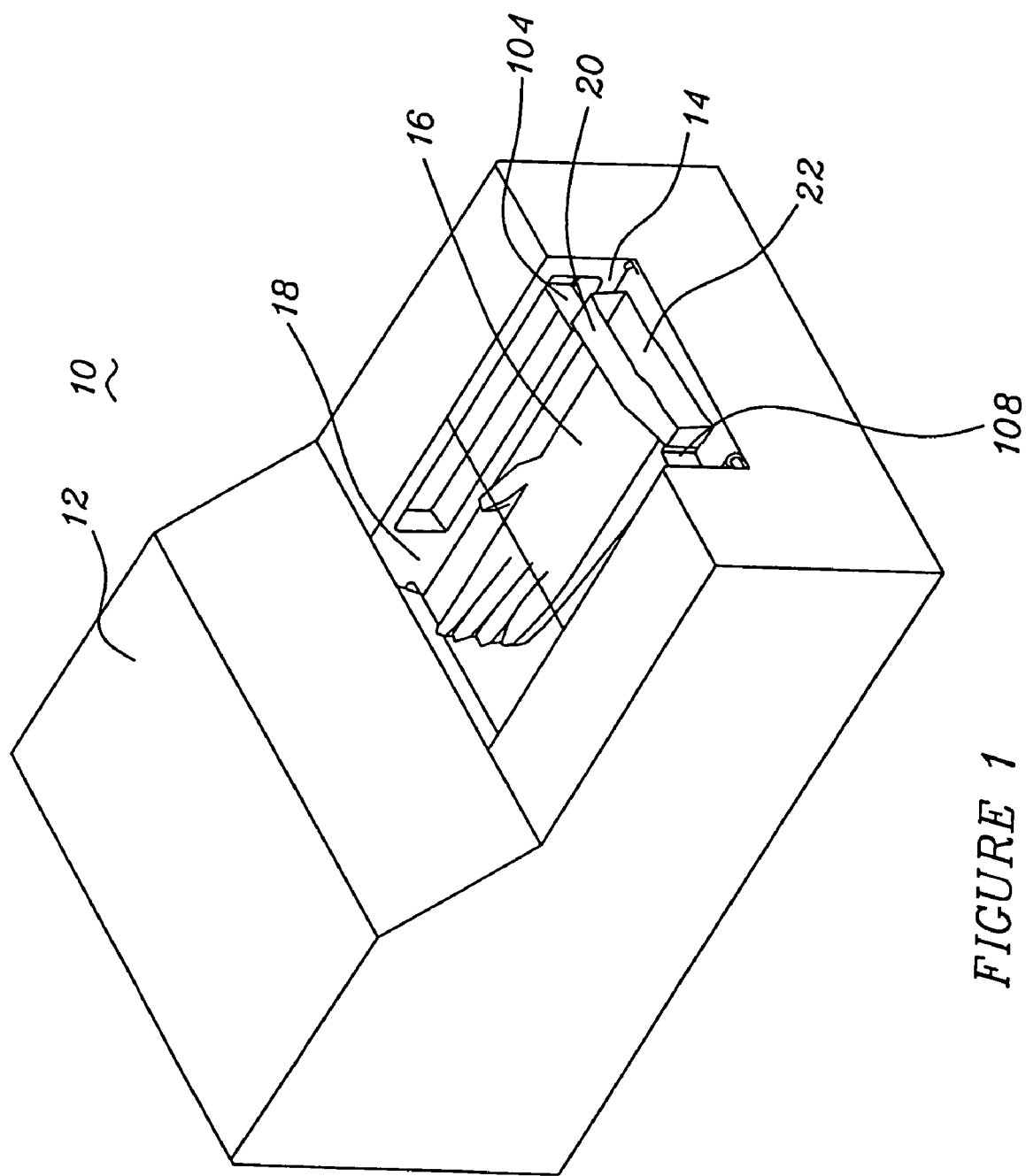
FIG. 1 is a perspective view of the glove donning apparatus of the instant invention.

FIG. 1 illustrates a glove donning apparatus 10 generally contained within a housing 12. Housing 12 has a glove dispensing opening 14 containing a glove 16 visible through a transparent plastic cover 18. Glove 16 has a cuff 20 surrounding a user hand opening 22 which will be described in greater detail herein below.

Figure 2:
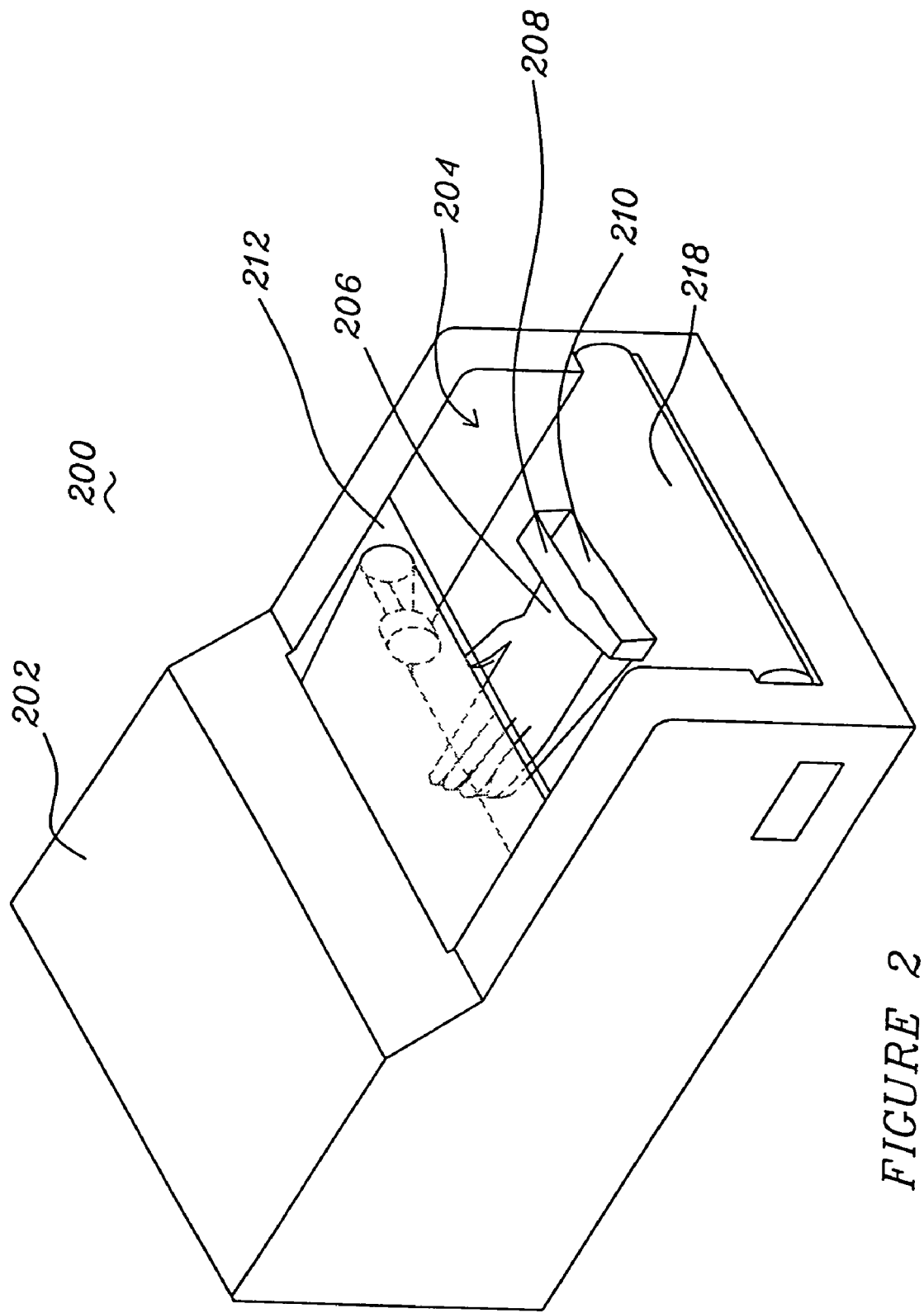
FIG. 2 is a perspective view of the glove removal apparatus of the instant invention.
Figure 2A:
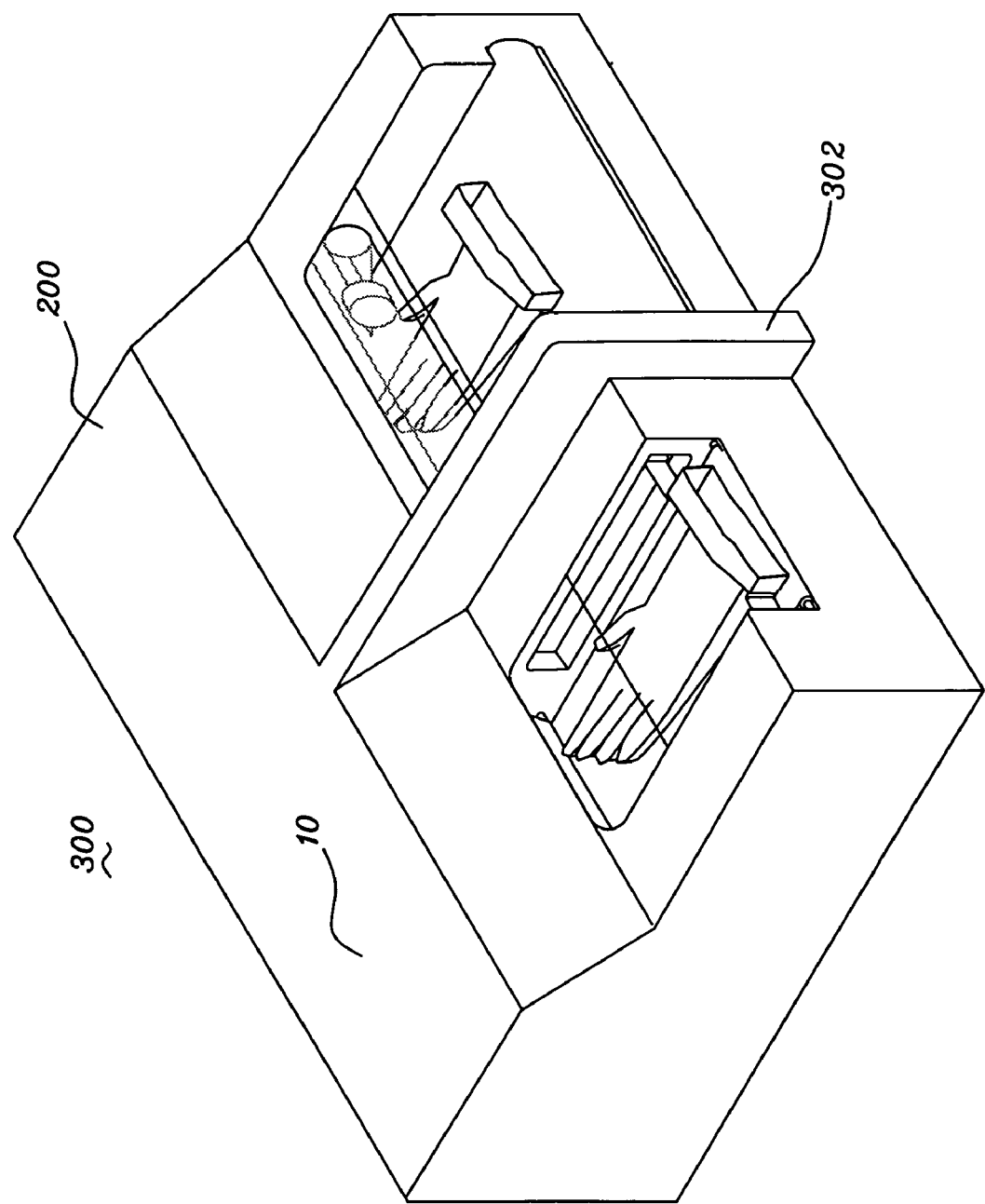
FIG. 2A is a perspective view showing the glove donning apparatus and the glove removal apparatus in a common housing.

A glove removal apparatus 200 contained within a housing 202 is disclosed in FIG. 2. Although glove donning apparatus housing 12 and glove removal apparatus housing 202 are shown separately, it is envisioned that the glove donning apparatus 10 and the glove removal apparatus 200 would be located in close proximity to each other and may reside adjacent to each other in a common housing 300 as shown in FIG. 2A. In FIG. 2A the common housing 300 is shown with a contamination barrier 302 separating the glove donning apparatus 10 and the glove removal apparatus 200. Glove removal housing 202 has a glove removal opening 204 at one end thereof. A glove 206 having a cuff 208 defining a user hand opening 210 is shown (without a user's hand inserted therein) at the glove removal opening 204 for removal from a user's hand, as will be described in greater detail herein below. Glove removal opening 204 is partially covered by a transparent plastic cover 212.

Details of the glove donning apparatus 10 may be seen by referring to FIGS. 4 through 11. Prior to being used, gloves 16 are encased and sealed in a carrier 23 comprising upper and lower feed sheets 24 and 26. Carrier 23 is wound onto a main feed reel 28 supported within in glove donning housing 12.

Figure 4:
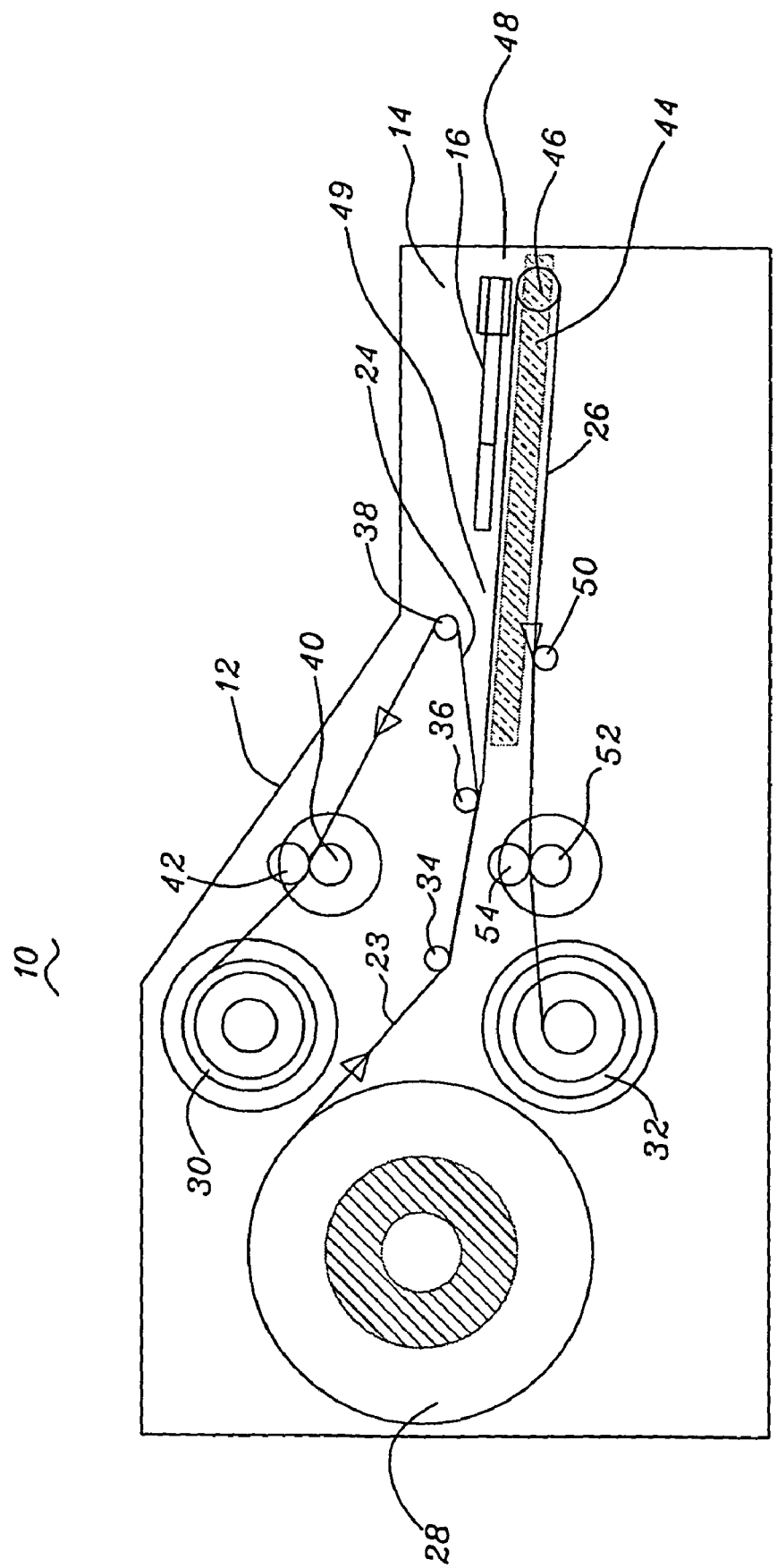
FIG. 4 is a schematic side view of the travel path of the feed roll sheets in the glove donning apparatus of the instant invention.
Figure 5:
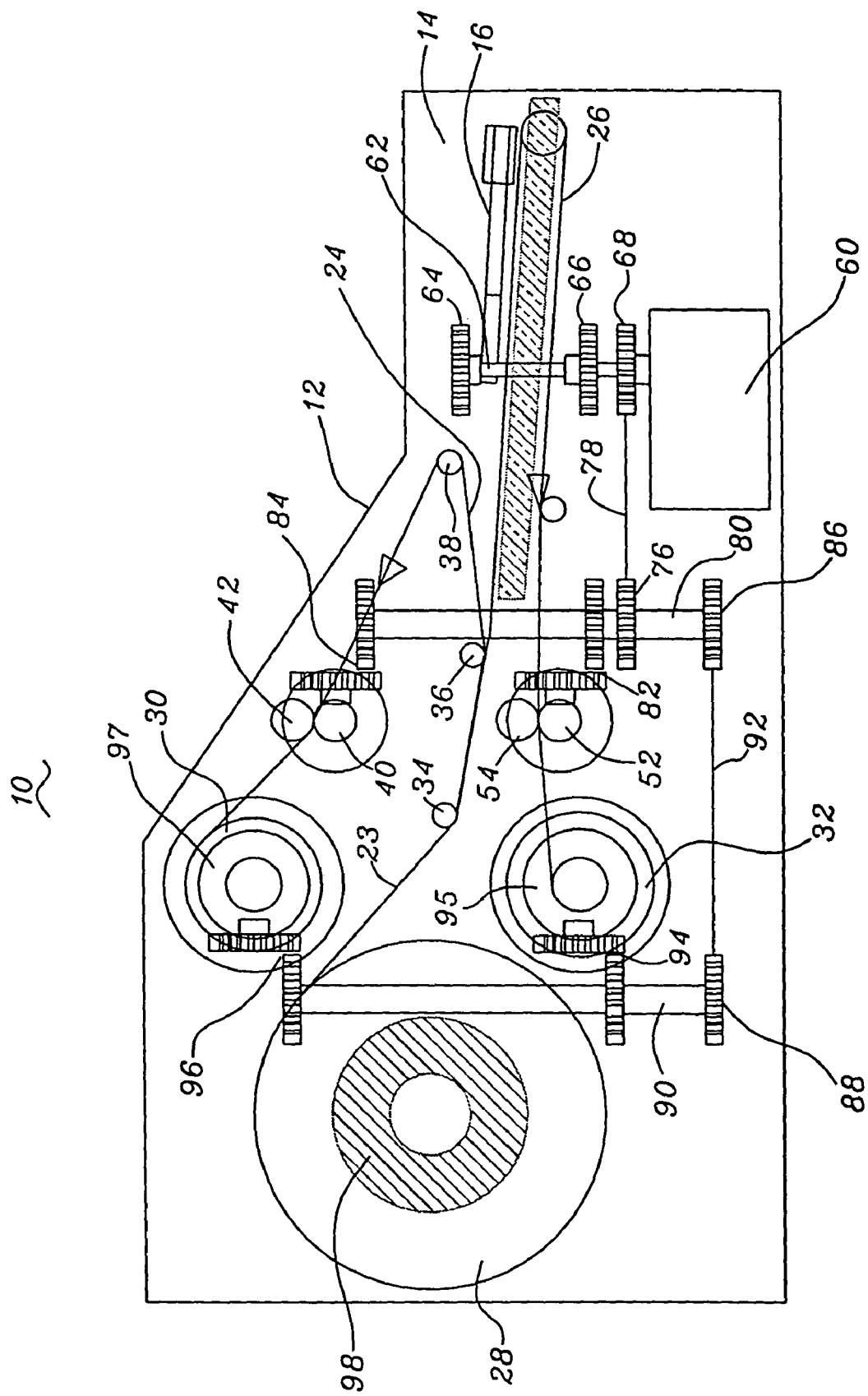
FIG. 5 is a schematic side view of the feed sheet drive mechanism for the glove donning apparatus of the instant invention.
Figure 6:
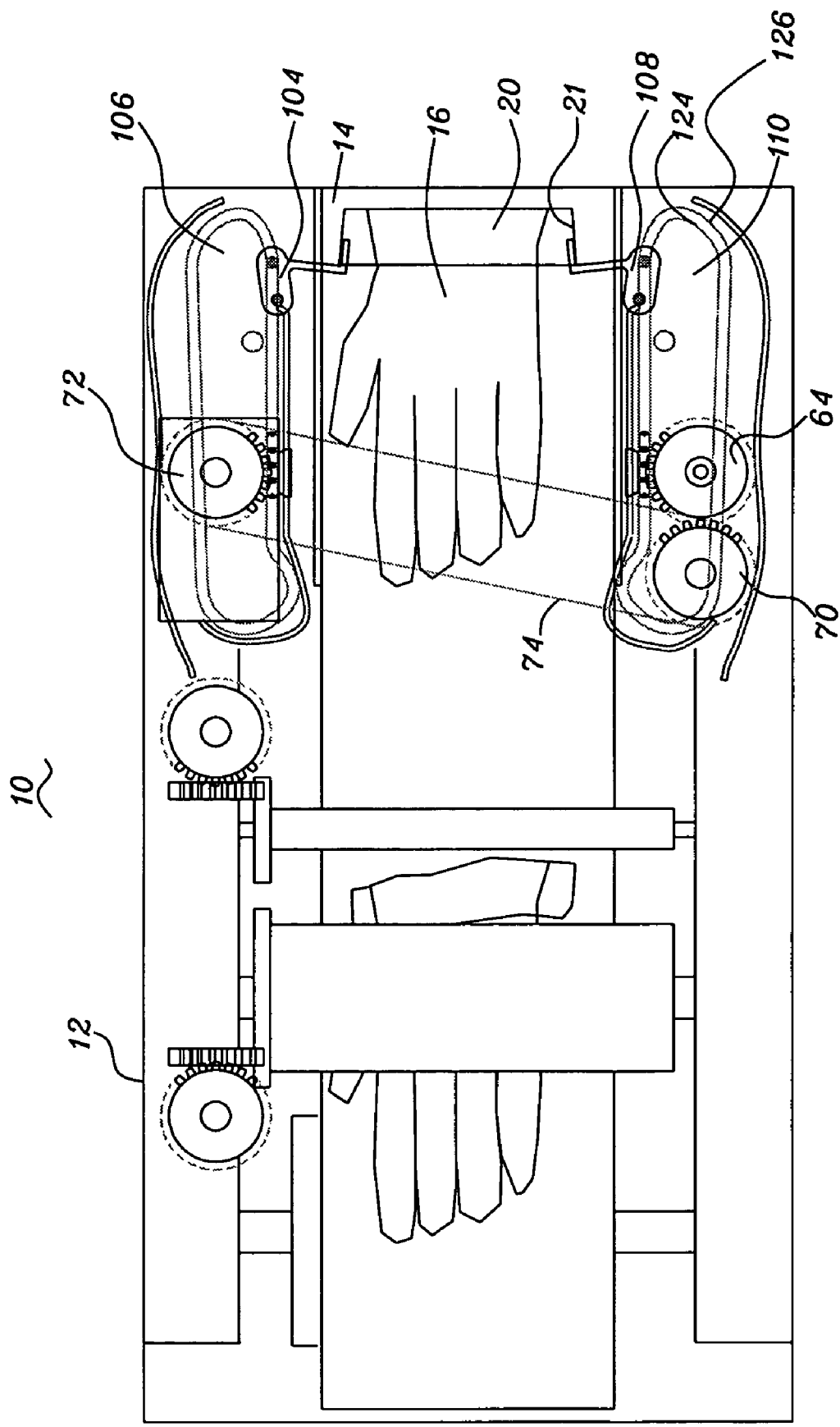
FIG. 6 is a partial top sectional view of the grabber mechanism of the glove donning apparatus.
Figure 7A:
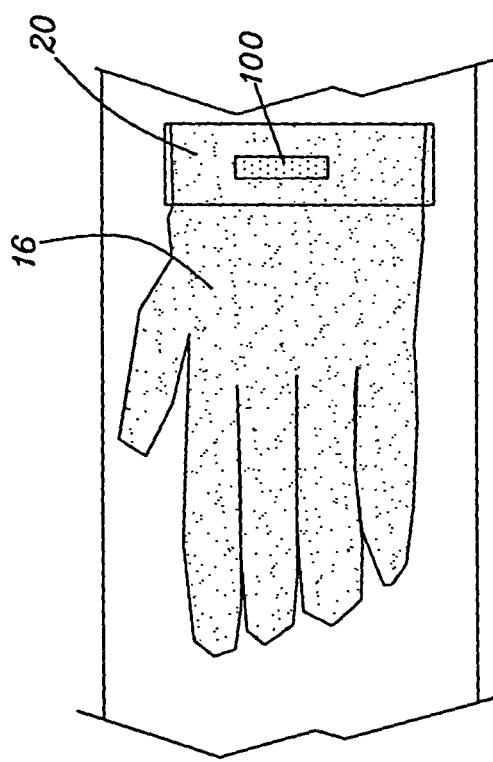
FIGS. 7A and 7B are plan views of a glove encased in upper and lower feed sheets as it travels towards a glove dispensing opening.
Figure 8A:
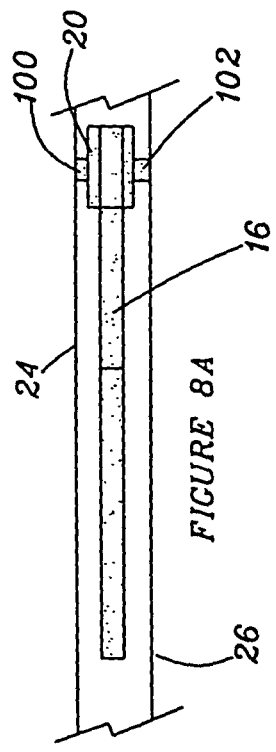
FIGS. 8A and 8B are schematic cross-sectional views of the gloves illustrated in FIGS. 7A and 7B respectively.
Figure 7B:
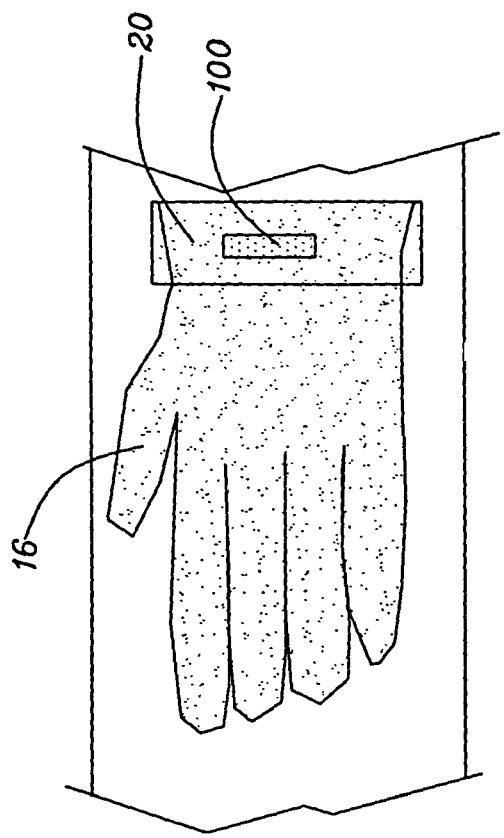
Figure 8B:
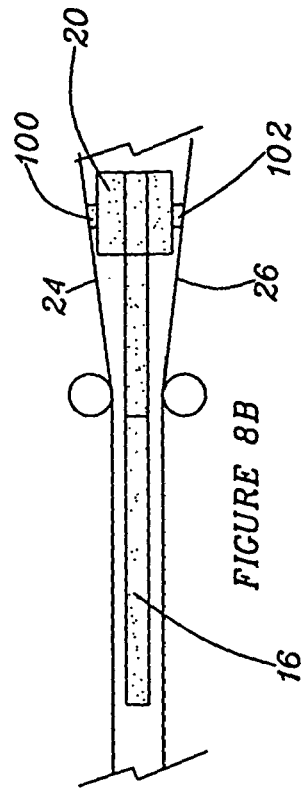

Carrier 23 containing gloves 16 is moved or conveyed from main feed reel 28 to glove dispensing opening 14 when a user wishes to don a glove by a mechanism which may be seen best by referring to FIGS. 4 and 5. It should be noted that when the glove donning apparatus 10 is actuated and the glove carrier 23 is moved toward the glove dispensing opening 14, upon reaching opening 14 upper feed sheet 24 is separated from lower feed sheet 26 and is wound onto an upper feed sheet take up reel 30 while lower feed sheet 26 is wound onto a lower feed sheet take up reel 32. In FIG. 4 it may be seen that glove carrier 23 is pulled or driven past idler roller 34 and idler roller 36 located at the rear end of glove dispensing opening 14. At idler roller 36, upper feed sheet 24 separates from lower feed sheet 26 and passes around idler roller 38 and between upper feed sheet drive roller 40 and upper feed sheet pinch roller 42 and onto upper feed sheet take up reel 30. Lower feed sheet 26 is fed or driven over a support plate 44 accessible through glove dispensing opening 14 around an idler roller 46 mounted at the outer end 48 of glove dispensing opening 14, around an idler roller 50 between a lower feed sheet drive roller 52 and a lower feed sheet pinch roller 54 and onto lower take up sheet reel 32. Movement of glove carrier 23 and upper and lower feed sheets 24 and 26, as depicted in FIG. 4, is through a series of drive shafts and gears depicted in FIG. 5. In order to move carrier 23 containing gloves 16, a user activates a prime mover 60. Prime mover 60 is a gearbox or transmission driven by a foot-operated pedal gear. The output of prime mover 60 drives shaft 62 containing gears 64, 66 and 68. In FIG. 6, it may be seen that gear 64 drives a left grabber drive, as will be described herein below. Gear 64 also drives a reverse gear 70 connected to a right grabber drive gear 72 through a drive belt 74. Turning again to FIG. 5, it may be seen that gear 68 is connected to a gear 76 through a drive belt 78 to thereby drive a shaft 80. Shaft 80 drives lower feed sheet drive roller 52 through a gear reduction unit 82 and drives upper feed sheet drive roller 40 through a gear reduction unit 84.

A gear 86 mounted on roller drive shaft 80 is drivingly connected to a gear 88 affixed to take up reel drive shaft 90 through a drive belt 92. Take up reel drive shaft 90 is connected to lower feed shaft take up reel 32 through a gear reduction unit 94 and a one-way slip clutch 95. Clutch 95 will slip to prevent over speeding. Take up reel drive shaft 90 is connected to upper feed sheet drive roller 30 through a gear reduction unit 96 and a one-way slip clutch 97. A friction clutch 98 acts to retard the rotation of main feed reel 28. This is to prevent the reel from over speeding as the glove carrier 23 is pulled away from it.

Turning to FIGS. 7A, 7B, 8A and 8B, it may be seen that an upper and lower adhesive strip 100 and 102 is affixed to the inner surface of the upper and lower feed sheets 24 and 26 such that the strips engage opposite sides of the cuff 20 of an encased glove 16. Consequently, when the upper and lower feed sheets 24 and 26 separate at the inner end 49 of the glove dispensing opening and move toward their respective upper and lower feed sheet take up reels 30 and 32, the top of the glove cuff 20 is moved away from the bottom of the glove cuff to provide a larger cuff pocket or opening for insertion of grabber arm tips 116 of grabber arms 104 and 108. Right grabber arm 104 of a right grabber drive 106 and left grabber arm 108 of a left grabber drive 110 simultaneously engage the inner surface 21 of a cuff 20 to secure the glove 16 to assist the user in donning the glove. Referring to FIG. 6, it may be seen that right grabber drive 106 is driven by gear 72 and left grabber drive 110 is driven by gear 64 mounted on grabber drive shaft 62. See detail in FIG. 11B. The operation of the right and left grabber arms 104 and 108 may be seen schematically by referring to FIGS. 9A and 9B and will be described in detail hereinafter. FIG. 10 depicts the operation of the left grabber drive 110. Details of left grabber arm 108 may be seen by referring to FIG. 11A. Left grabber arm 108 has a base 112 having an upwardly projecting member 114 with an L-shaped grabber arm tip 116 at the outer end thereof. A grabber roller cam follower 118 is mounted on grabber arm base 112 adjacent a spring biased grabber track follower shaft 120. Grabber track roller shaft 120 is mounted with a grabber arm base bearing 136 to allow the grabber arm base 112 to rotate. A torsion spring 122 acts to bias grabber arm 108 in a counterclockwise direction, as depicted in FIG. 10. Grabber track follower shaft 120 has an attached chain segment 135. Grabber track follower chain segment 135 is attached to grabber drive chain 124. As mentioned above, FIG. 10 describes the operation of left grabber drive 110. Gear 64 of left grabber drive 110 drives chain 124 which pulls grabber arm 108 and causes grabber track follower shaft 120 at the inner end of grabber arm base 112 to be driven within a track 126. Chain 124 is mounted in track 126. At the same time, torsion spring 122 causes grabber arm 108 to rotate counterclockwise such that grabber roller cam follower 118 rides on inside and outside cam track 128 and 130.

Because the right and left grabber drives 106 and 110 and the right and left grabber arms 104 and 108 operate in exactly the same manner on opposite sides of a glove in the glove donning apparatus 10, this description will proceed with respect to grabber arm 108 with the understanding that it also applies to grabber arm 104 of right grabber drive 106.

Figure 9A:
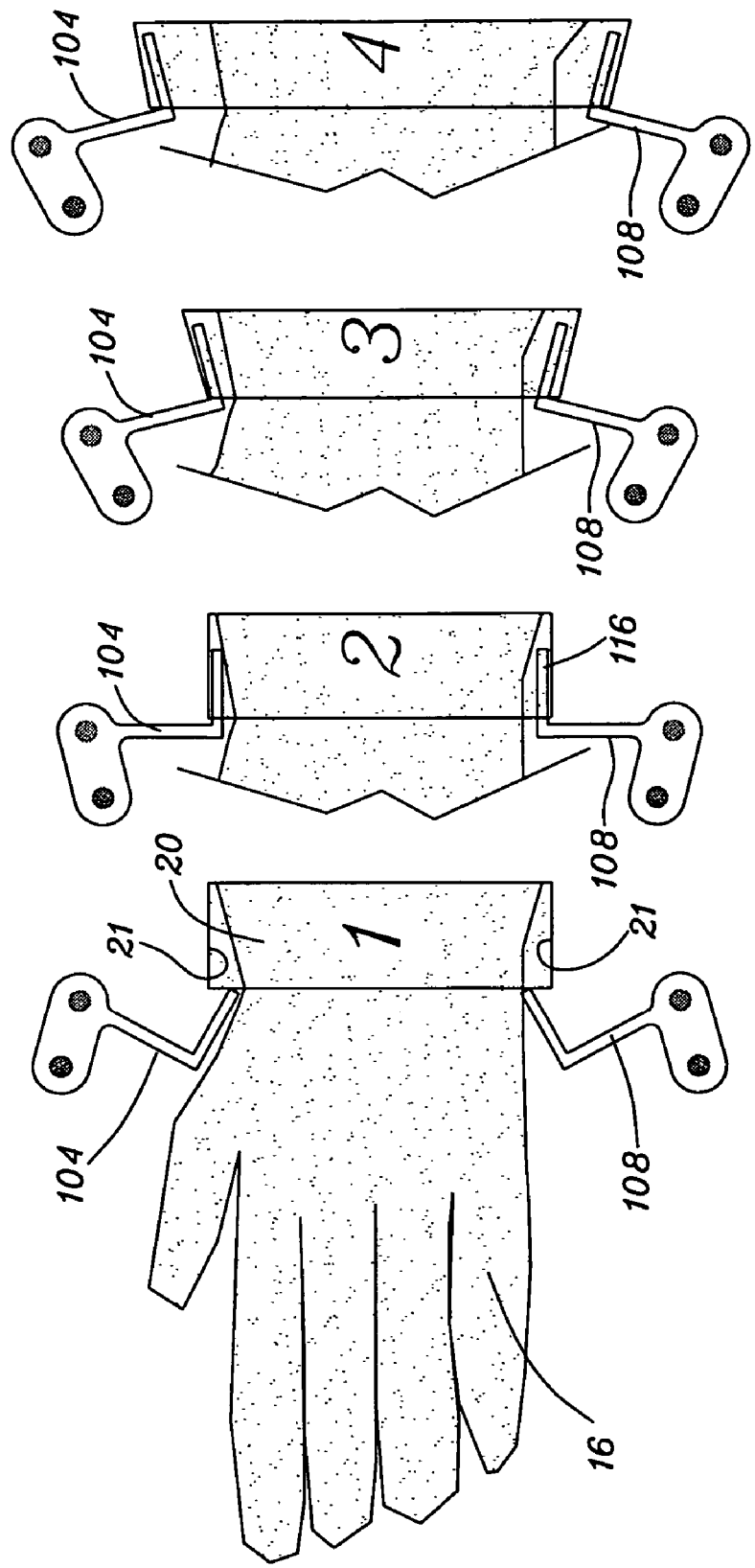
FIGS. 9A and 9B are a schematic illustration of the sequence of movements for one cycle of operation of the grabber arms with respect to a glove cuff during glove donning.
Figure 9B:
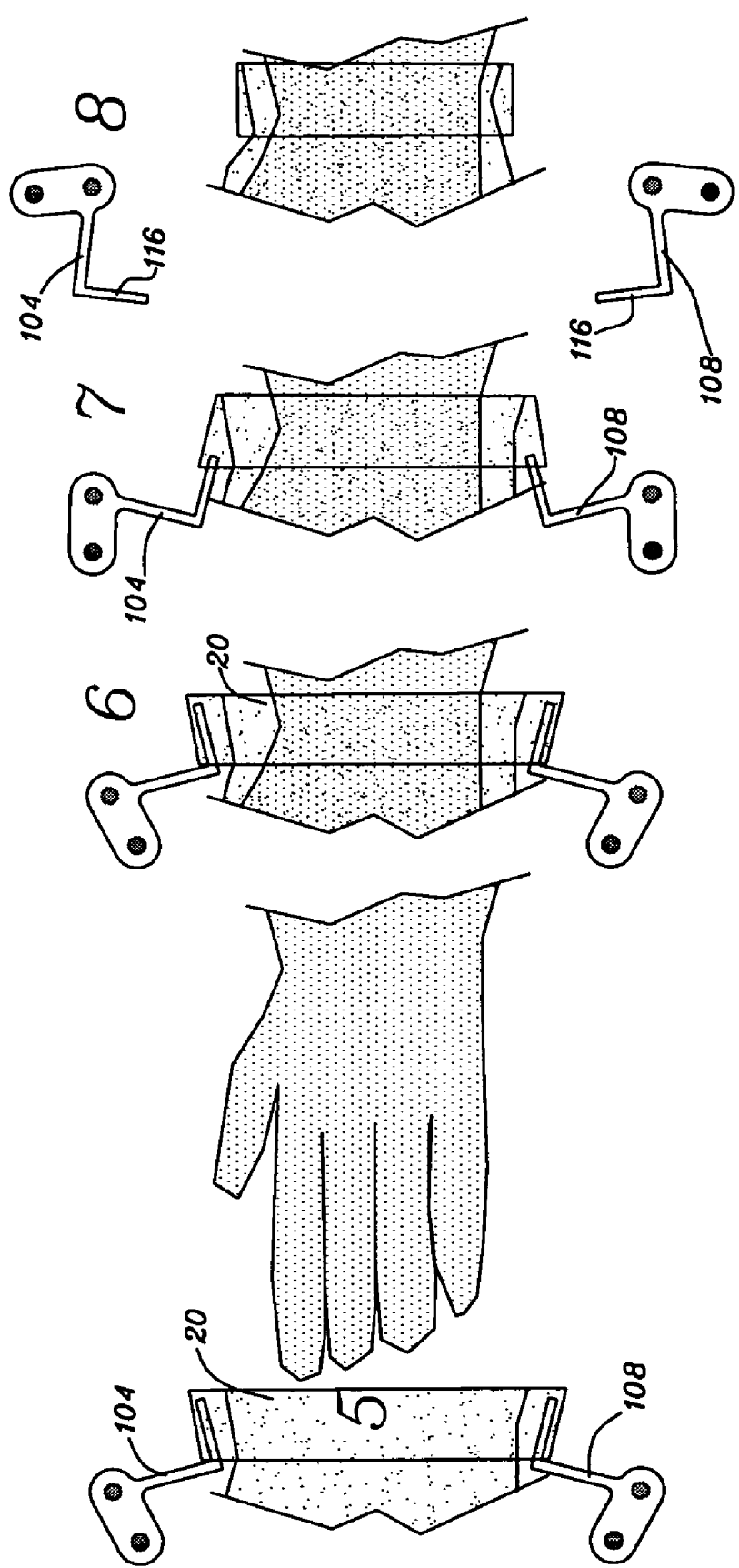
Figure 10:
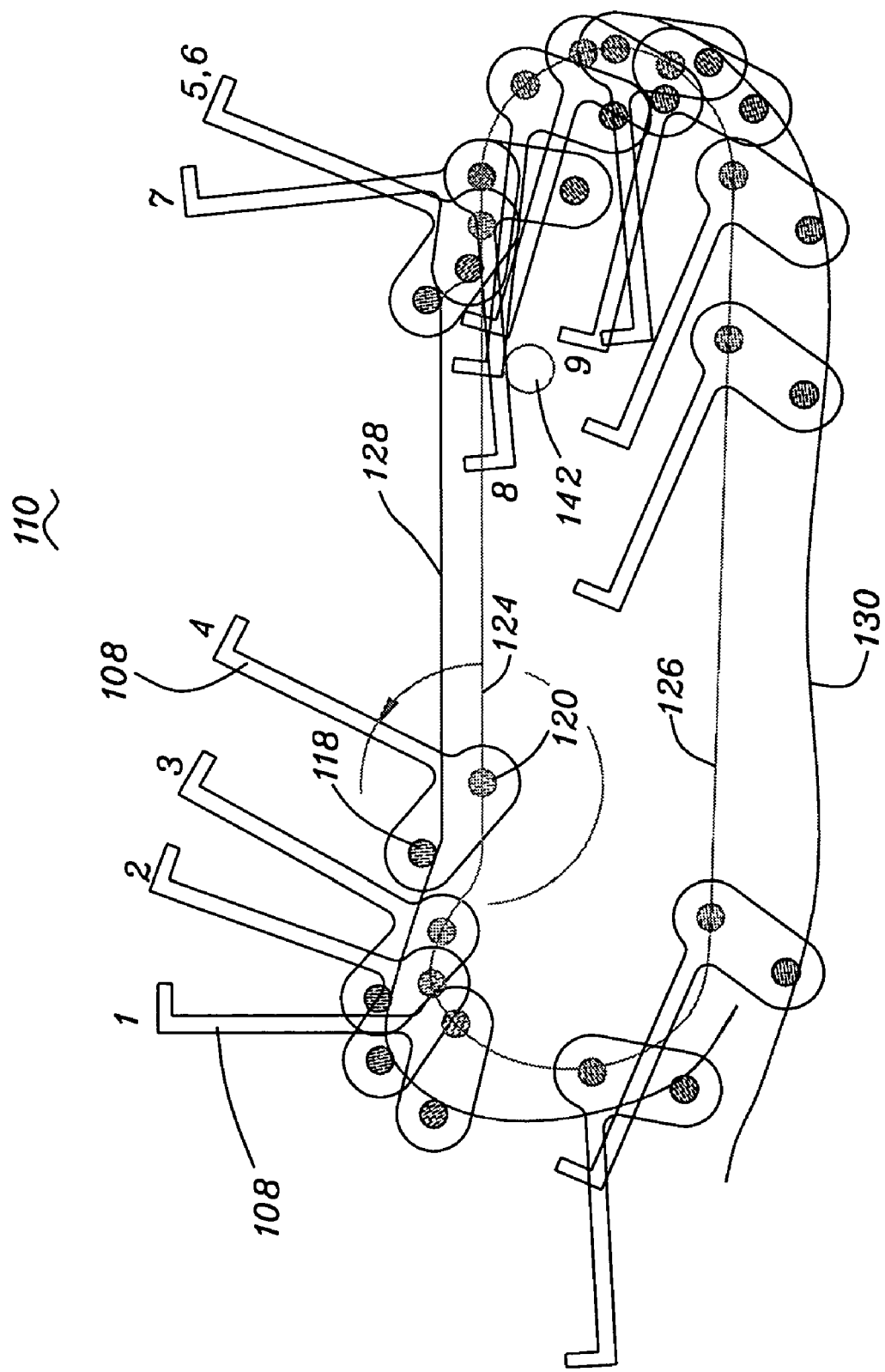
FIG. 10 is a schematic plan view of the left side grabber arm drive mechanism in the glover donning apparatus.
Figure 11B:
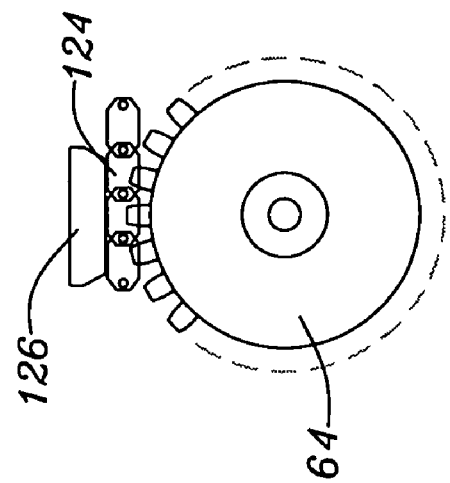
FIG. 11B illustrates the chain and sprocket drive for the grabber arm drive mechanisms of the glove donning apparatus.
Figure 11A:
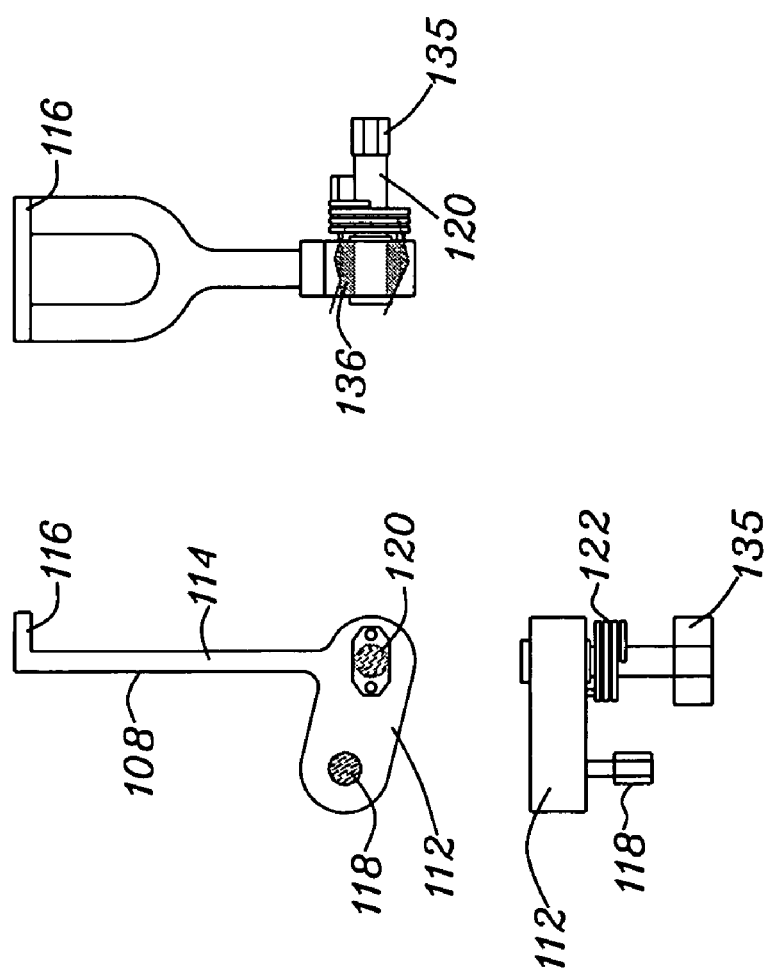
FIG. 11A depicts side, end and plan views of a grabber arm in the glove donning apparatus.
Figure 12:
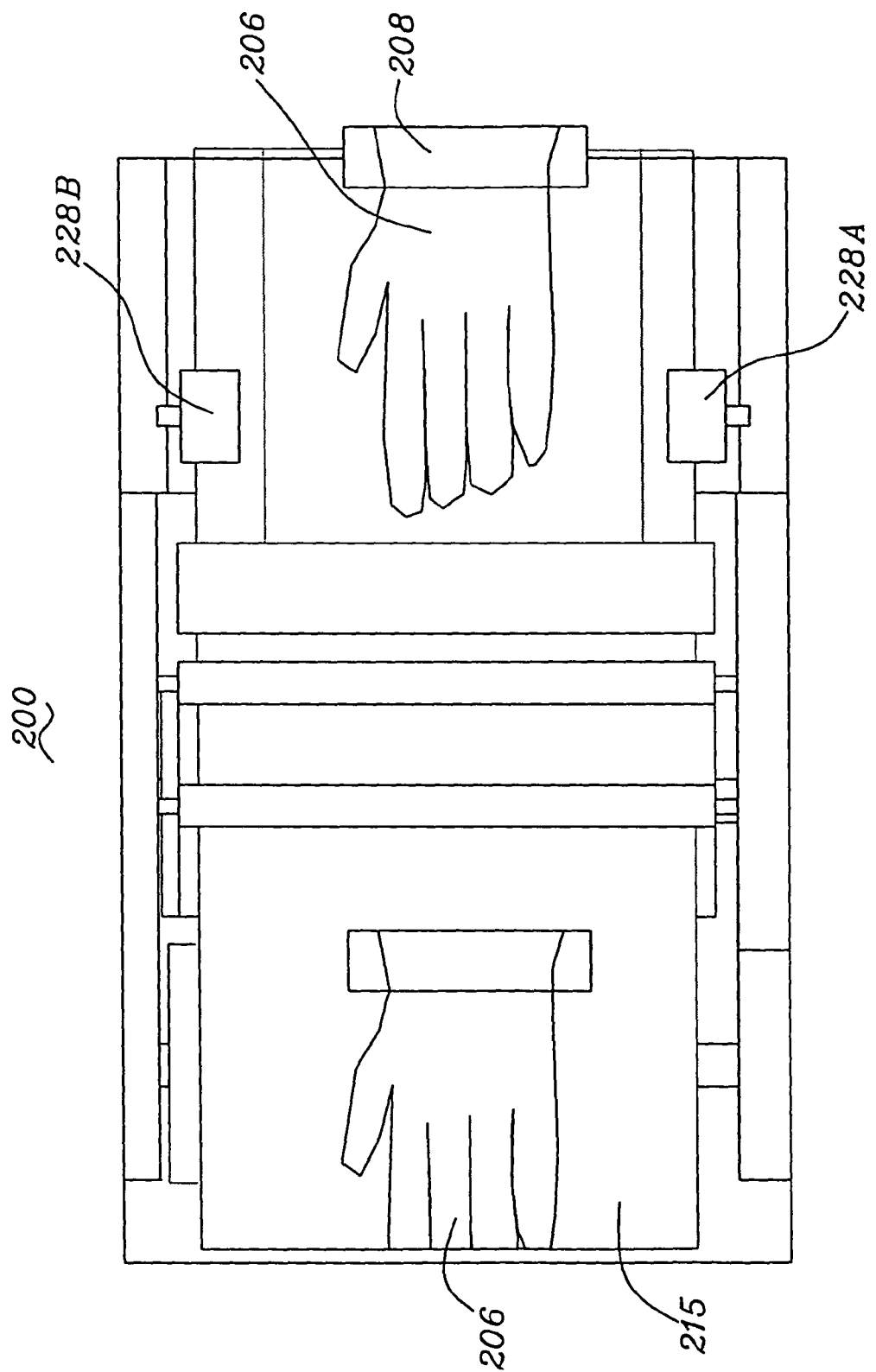
FIG. 12 is a schematic plan view of the movement of a glove during glove removal in the glove removal apparatus of the instant invention.
Figure 13:
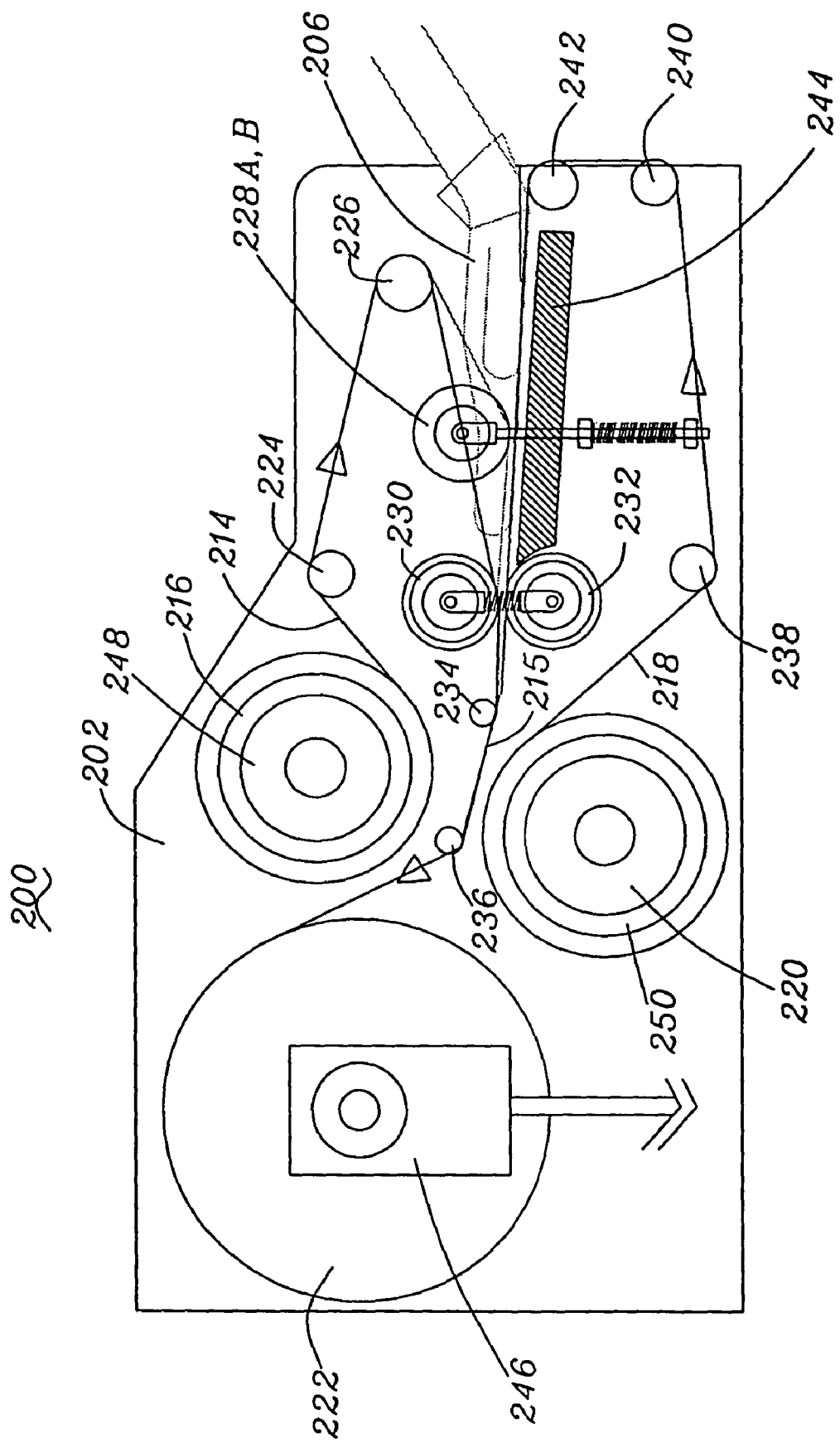
FIG. 13 is a schematic view of the travel path of the top and bottom feed roll sheets in the glove removal apparatus.

Turning to FIGS. 9A and 9B, in position 1, grabber arm tip 116 of arm 108 begins to enter the inner surface 121 of cuff 20. It is just prior to this position that the upper and lower feed sheets 24 and 26 begin to diverge at the inner end 49 of glove dispensing opening 14 and the top surface of cuff 20 is lifted away from the bottom surface of cuff 20 to enable the grabber arm tip 116 to engage the inner surface 21 of the cuff 20. In position 2, grabber arm tip 116 is fully engaged in the inner surface 21 of cuff 20. In position 3, the grabber arm 108 rotates away from the center of glove 16 to prevent the glove 16 from slipping off grabber arm tip 116. In position 4, the grabber arms 108 and 104 move away from the centerline of the glove 16 to maximize the glove opening. Position 5 shows the glove after it has moved near the end of the glove dispensing opening 48 and is now ready for the user to insert a hand into the fully secured and open glove 16. Position 6 shows the hand inserted into the glove 16 at position 5. At positions 7 and 8, grabber arm 108 rotates counterclockwise away from cuff 20 and stops against grabber arm stop 142. Subsequently, as the grabber arm assembly moves along grabber track 126, the arm tip 116 slips past grabber arm stop 142 (position 9, FIG. 10) and allows cam follower 118 to rest against outer cam track 130. Note that the cam follower 118 must be above the grabber track 126 to allow the grabber arm assembly to rotate counterclockwise over the grabber track 126. Subsequent to the user's hand entering the glove, the grabber arm 108 is rotated counterclockwise (positions 7 and 8) to allow the cuff 20 to slip off the grabber tip end 116 and separate the grabber arm from the glove cuff inasmuch as the donning operation has been completed. Note that the grabber arm tip 116 remains at a distance from the inserted hand to prevent contact during the glove release action.

Thereafter, the left grabber drive 110 moves the left grabber arm 108 back to initial position 1.

It should be noted that the upper and lower adhesive strips 100 and 102 are firmly affixed to the inner surface of the upper and lower feed sheets 24 and 26. This is important because after the glove is removed from the upper and lower feed sheets, the adhesive strips stay on the feed sheets and no adhesive remains on the glove to prevent the glove from picking up unwanted debris. Additionally, the adhesive strip surface on the glove ends up being on the inside of the glove away from outside media, should any residual adhesive be left.

It should be noted that the adhesive strips 100 and 102 are not being used to open the glove for donning. They are being used to lightly pull the top of the glove cuff up which causes the glove cuff sides to open for presentation to the grabber arms 104 and 108. Thus, the adhesive can have a very light tack such that it will allow the upper and lower feed sheets 24 and 26 to easily separate from the glove cuff 20.

For the right and left grabber drives 106 and 110 to operate properly, the gloves must be positioned properly with respect to the right and left grabber arms 104 and 108 when the grabber arms are at the initial or first position of travel. Once the grabber arms 104 and 108 engage the cuffs 20 of a glove 16 the glove moves independently of the upper and lower feed sheets 26 and 24. To accomplish this, the upper and lower feed sheet drive rollers 40 and 52 must be synchronized with the right and left grabber drives 106 and 110. In order to have the right and left grabber drives synchronized with the speed of the upper and lower feed sheet drive rollers 40 and 52, the grabber drive shaft 62 and the drive roller drive shaft 80 must rotate at a fixed rate with respect to each other. Because the upper and lower feed sheet take up reels 30 and 32 must be driven at ever decreasing speeds as the upper and lower take up sheets 24 and 26 are wound thereon due to their increasing diameters, the speed of carrier 23 cannot be determined by the speed of the take up reels 30 and 32. For this reason, the take up reels 30 and 32 are driven at a faster speed than the upper and lower feed sheet drive rollers 40 and 52 and the one-way slip clutches 95 and 97 allow the speed of the take up reels 30 and 32 to go at whatever speed is required to maintain the proper tension of the upper and lower feed sheets.

FIGS. 2, 3, 12, 13 and 14 depict the operation of the glove removal apparatus 200 of the instant invention.

The function of the glove removal apparatus 200 is to assist a user in removing a disposable glove 206 without touching the external surface of the glove and without creating an aerosol or splatter on removal and thereafter encasing the used glove 206 in a carrier such that it is isolated from the user and the atmosphere until it can safely be disposed.

To this end, a top feed sheet 214 is wound on a top feed roll 216, a bottom feed sheet 218 is wound on a bottom feed roll 220 and the two feed rolls 216 and 220 are rotatably mounted within a glove removal housing 202. The top and bottom feed sheets 214 and 218 have a sticky side adapted to engage a glove 206 as will be described hereinafter. The top and bottom feed sheets 214 and 218 are connected to and driven by a take up reel 222. A manually operated prime mover 246 such as a treadle-driven gearbox is affixed to and drives take up reel 222. Top feed sheet 214 passes around idler rollers 224 and 226 under a pair of spring biased side rollers 228A and 228B, between a pair of compression rollers 230 and 232, around a pair of idler rollers 234 and 236 and onto take up reel 222. Bottom feed sheet 218 passes around idler rolls 238, 240 and 242 over a backup plate 244 adjacent glove removal opening 204, between compression rollers 230 and 232 where it merges with top feed sheet 214 to form a sealed glove carrier 215 and passes around idler rollers 234 and 236 onto take up reel 222. Friction clutches 248 and 250 are affixed to upper and lower feed sheet rolls 216 and 220 to prevent them from over speeding when they are being driven by the take up reel 222.

Figure 14:
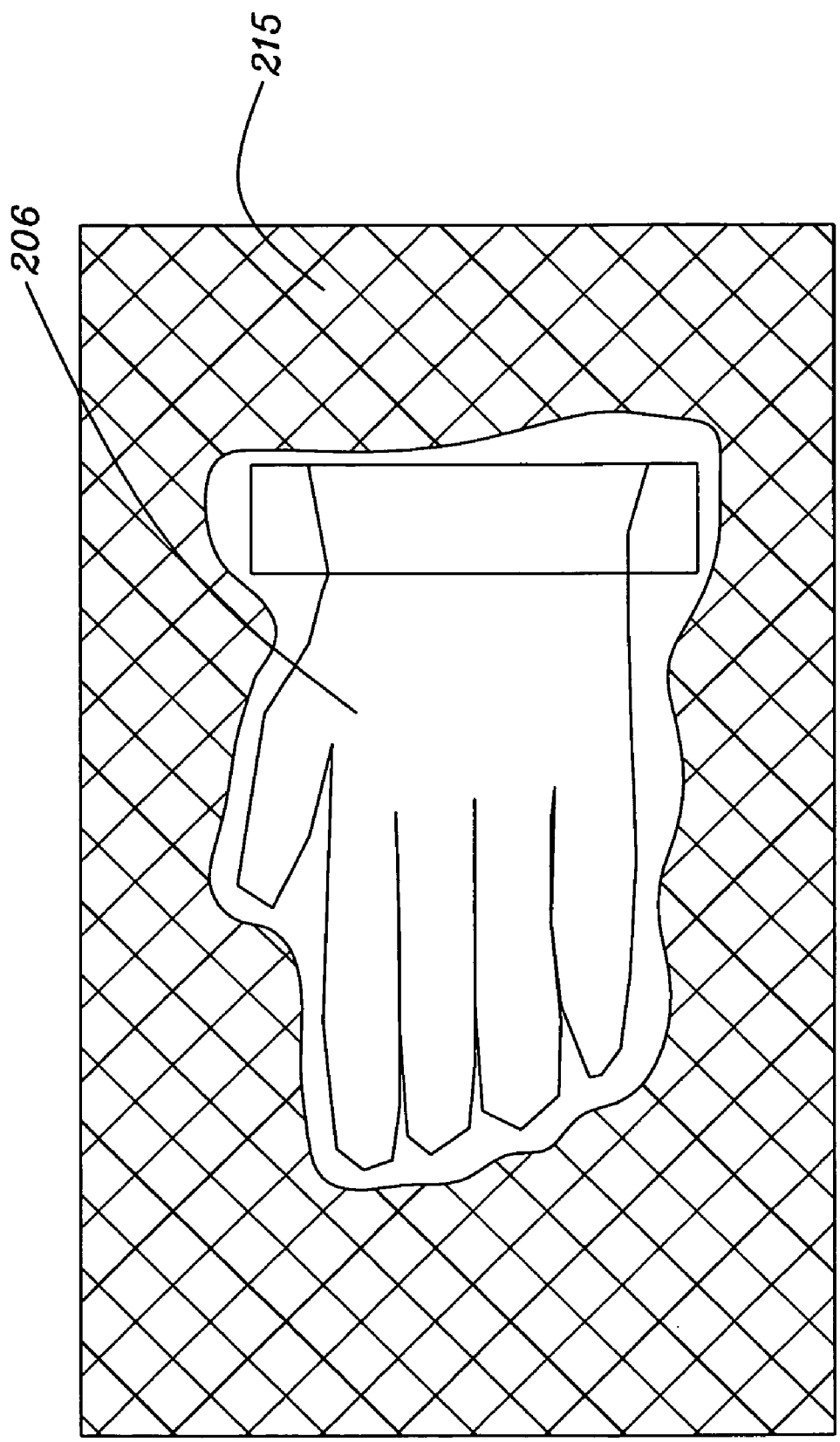
FIG. 14 is a partial plan view of a glove encased between top and bottom feed roll sheets subsequent to glove removal.

In order to operate the glove removal apparatus 200, a user lays a gloved hand on the carrier sheet 218 which passes over back up plate 244 at the glove removal opening 204. The sticky bottom feed roll sheet 218 engages one surface of the glove and moves it towards the sticky side of the top feed roll sheet 214 and between the side rollers 228A and 228B which causes top feed roll 214 to engage the top surface of the glove 206. When the glove 206 contacts the sticky surfaces of the top and bottom feed roll sheets 214 and 218, the glove is pulled from the hand of the user. Thereafter, the glove is encased between the upper and lower feed sheets 214 and 218 to form the sealed glove carrier 215 which is wound upon take up reel 222 for subsequent disposal, as illustrated in FIG. 14.

Figure 3:
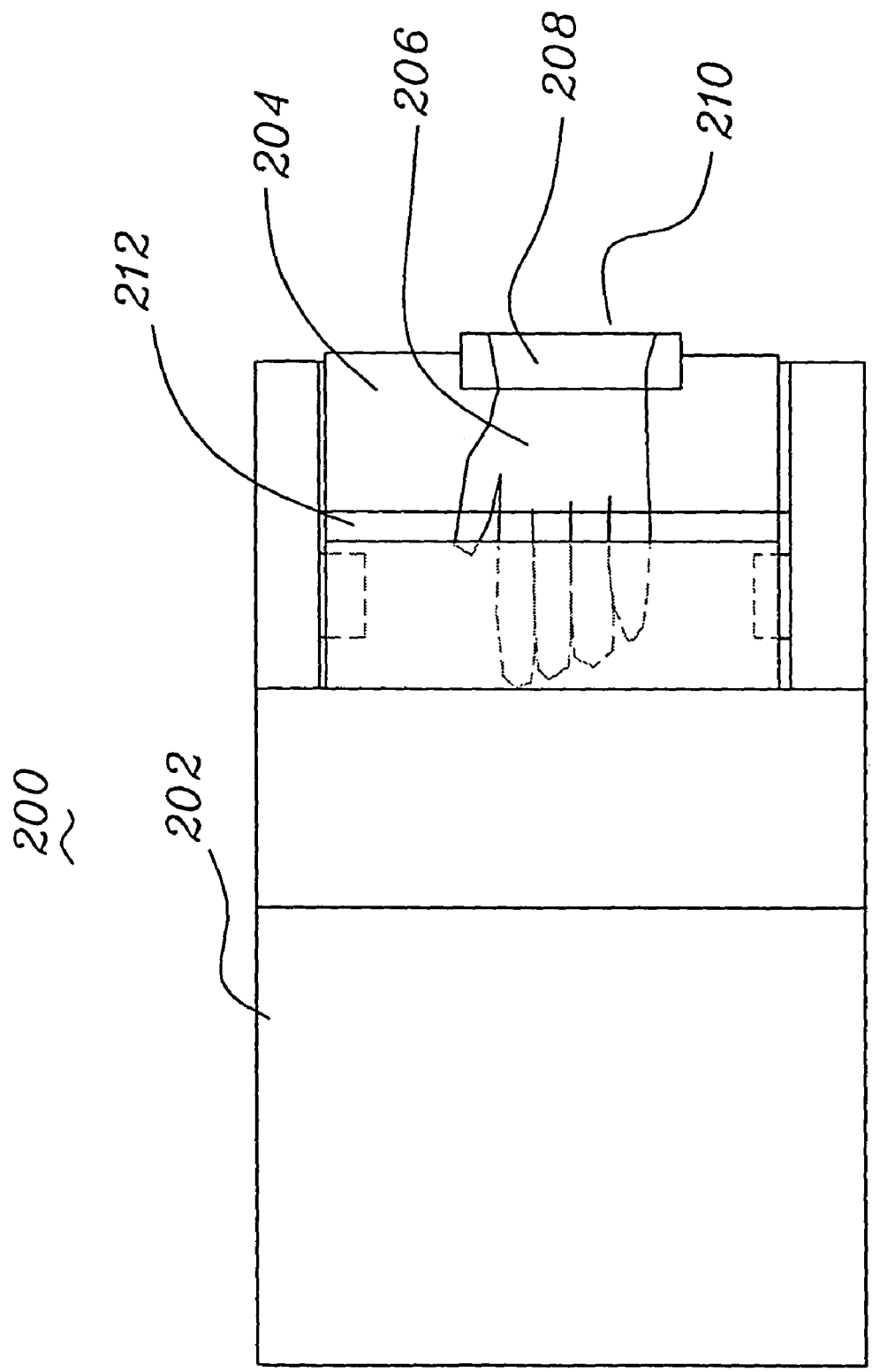
FIG. 3 is a plan view of the glove removal apparatus shown in FIG. 2.

In FIGS. 2 and 3, it may be seen that the transparent glove cover 212 enables a user to see the gloved hand at all times during the glove removal procedure. This is advantageous, as people are hesitant to put their hands into a machine if they cannot see what is happening.

Additionally, the side rollers 228A and 228B and the final pinch rollers 230 and 232 are spring loaded and made of soft material that could not cause injury if a hand were trapped therebetween but are stiff enough to exert sufficient force to guide the sticky surface of the top and bottom feed roll sheets 214 and 218 to remove a glove from a hand. It is estimated that the proper spring setting force is between ½ and 1½ pounds.

From the above, it may be seen that the glove removal apparatus 200 of the instant invention allows removal of the glove without requiring the user to touch the outside of the glove, allows removal of the glove without assistance, and seals the glove in an air-tight, sanitary carrier for the proper disposal.

Various changes may be made to the size, shape, and relative proportions of the different invention elements disclosed and described herein without departing from the scope, meaning, or intent of the claims which follow.

We claim:

1. A glove dispensing and donning apparatus comprising:
    a housing having a glove dispensing opening;
    a feed roll having a spaced pair of upper and lower feed sheets at least partially received within said housing;
    a glove having a cuff defining a hand opening sandwiched between said upper and lower feed sheets;
    a feed sheet drive for advancing said upper and lower feed sheets and said glove toward said glove dispensing opening;

a pair of grabbers each having a base and an arm affixed to said base positioned one on each side of said feed roll; and a grabber drive connected to said grabbers which moves said grabber arms into engagement with said glove cuff, rotates said grabber arms towards each other to secure said glove and then moves said grabber arms apart to cause said glove hand opening to expand to enable a user to easily insert a hand into said glove hand opening, and rotates said grabber arms away from each other to withdraw said grabber arms from said glove cuff to release said glove after a user's hand has been inserted into said glove.

2. The glove dispensing and donning apparatus of claim 1, further comprising;

an adhesive on each of said upper and lower feed sheets which engages opposite sides of said glove cuff to lift said glove cuff to enable said grabbers to engage said cuff as said glove is advanced toward said glove dispensing opening.

3. The glove dispensing and donning apparatus of claim 1, further comprising an upper take-up roll for receiving said upper feed sheet and a lower take-up roll for receiving said lower feed sheet after said upper and lower feed sheets have advanced beyond said glove dispensing opening.

4. The glove dispensing and donning apparatus of claim 3, further comprising an upper and lower take-up roll drive and wherein said upper and lower take up rolls are driven at different speeds than said upper and lower feed sheets.

5. The glove dispensing and donning apparatus of claim 1, said grabber drive further comprising;

a first drive chain affixed to the base of a grabber on one side of said feed roll upper and lower feed sheets and a second drive chain affixed to the base of a grabber on the other side of said feed roll upper and lower feed sheets.

6. The glove dispensing and donning apparatus of claim 5, further comprising:

a roller cam follower affixed to the base of each of said grabbers and a first cam on said one side of said feed roll upper and lower feed sheets which engages the grabber driven by said first drive chain and a second roller cam on said other side of said feed roll upper and lower feed sheets which engages the grabber driven by said second drive chain.

7. The glove dispensing and donning apparatus of claim 1, wherein said feed sheet drive comprises upper and lower feed sheet drive rollers which pull said upper and lower feed sheets from said feed roll.

8. The glove dispensing and donning apparatus of claim 7, further comprising a friction clutch connected to said feed roll to retard movement of said feed roll as said upper and lower feed sheets are pulled from said feed roll.

9. The glove dispensing and donning apparatus of claim 1, further comprising a prime mover having an output which drives said feed sheet drive and said grabber drive at a constant speed with respect to each other.

10. A glove removal apparatus comprising:

a housing having a glove removal opening;

a glove removal surface adjacent said glove removal opening;

a top feed roll having a top feed sheet and a bottom feed roll having a bottom feed sheet with said top and bottom feed sheets at least partially received in said glove removal opening;

an adhesive coating formed on top and bottom feed sheets;

guides causing said bottom feed sheet to pass over said glove removal surface;

guides causing said top feed sheet to pass above said glove removal surface;

guides causing said top and bottom feed sheets to converge in said glove removal opening such that said adhesive coated top and bottom feed sheets cooperate to strip a glove from a user's hand when said hand is placed on said glove removal surface in said glove removal opening such that it rests on said bottom feed sheet; and wherein said glove is encased between said top and bottom feed sheets subsequent to being removed from the hand of a user.

11. A glove removal apparatus comprising:

a housing having a glove removal opening;

a glove removal surface adjacent said glove removal opening;

a top feed roll having a top feed sheet and a bottom feed roll having a bottom feed sheet with said top and bottom feed sheets at least partially received in said glove removal opening;

an adhesive coating formed on top and bottom feed sheets;

guides causing said bottom feed sheet to pass over said glove removal surface;

guides causing said top feed sheet to pass above said glove removal surface;

guides causing said top and bottom feed sheets to converge in said glove removal opening such that said adhesive coated top and bottom feed sheets cooperate to strip a glove from a user's hand when said hand is placed on said glove removal surface in said glove removal opening such that it rests on said bottom feed sheet;

wherein said glove is encased between said top and bottom feed sheets subsequent to being removed from the hand of a user; and a take-up reel for storing said top and bottom feed sheets containing the encased gloves after they have passed through said glove removal opening.

12. The glove removal apparatus of claim 11, further comprising:

a prime mover drivingly connected to said take-up reel for pulling said top and bottom feed sheets from their respective top and bottom feed rolls through said glove removal opening and winding said top and bottom feed sheets onto said take-up reel.

13. The glove removal apparatus of claim 12, further comprising a friction clutch connected to each of said top and bottom feed rolls to retard movement of said top and bottom feed rolls as said top and bottom feed sheets are pulled from said feed rolls.

14. A glove removal apparatus comprising:

a housing having a glove removal opening;

a glove removal surface adjacent said glove removal opening;

a top feed roll having a top feed sheet and a bottom feed roll having a bottom feed sheet with said top and bottom feed sheets at least partially received in said glove removal opening;

an adhesive coating formed on top and bottom feed sheets;

guides causing said bottom feed sheet to pass over said glove removal surface;

guides causing said top feed sheet to pass above said glove removal surface;

guides causing said top and bottom feed sheets to converge in said glove removal opening such that said adhesive coated top and bottom feed sheets cooperate to strip a glove from a user's hand when said hand is placed on said glove removal surface in said glove removal opening such that it rests on said bottom feed sheet;

wherein said glove is encased between said top and bottom feed sheets subsequent to being removed from the hand of a user; and wherein said guides for said top feed sheet comprise a pair of side rolls that bias said top feed sheet downwardly into engagement with the top surface of a user's gloved hand in said glove removal opening.

15. A glove donning and removal apparatus comprising:
a housing having a glove dispensing opening and a glove removal opening;
a primary feed roll having a spaced pair of upper and lower feed sheets at least partially received within said housing;
a glove having a cuff defining a hand opening sandwiched between said upper and lower feed sheets;
a feed sheet drive for advancing said upper and lower feed sheets and said glove toward said glove dispensing opening;
a pair of grabbers each having a base and an arm affixed to said base positioned one on each side of said feed roll;
a grabber drive connected to said grabbers which moves said grabber arms into engagement with said glove cuff, rotates said grabber arms towards each other to secure said glove and then moves said grabber arms apart to cause said glove hand opening to expand to enable a user to easily insert a hand into said glove hand opening, and rotates said grabber arms away from each other to withdraw said grabber arms from said glove cuff to release said glove after a user's hand has been inserted into said glove;
a glove removal surface adjacent said glove removal opening;
a secondary top feed roll having a top feed sheet and a secondary bottom feed roll having a bottom feed sheet at least partially received in said glove removal opening;
an adhesive coating formed on one side of the top and bottom feed sheets;
guides causing said bottom feed sheet to pass over said glove removal surface;
guides causing said top feed sheet to pass above said glove removal surface;
guides causing said top and bottom feed sheets to converge in said glove removal opening such that said adhesive coated top and bottom feed sheets cooperate to strip a glove from a user's hand when said hand is placed on said glove removal surface in said glove removal opening such that it rests on said bottom feed sheet;
wherein said glove is encased between said top and bottom feed sheets subsequent to being removed from the hand of a user.

16. The glove donning and removal apparatus of claim 15, further comprising;
a storage roll; and
a storage roll drive for winding said top and bottom feed sheets containing the encased gloves onto said storage roll after they have passed through said glove removal opening.

17. The glove donning and removal apparatus of claim 15, further comprising;
a tacky strip on each of said upper and lower feed sheets which engages opposite sides of said glove cuff to lift said glove cuff to enable said grabbers to engage said cuff as said glove is advanced toward said glove dispensing opening.

18. The glove donning and removal apparatus of claim 15, further comprising;
an upper take-up roll for receiving said upper feed sheet and a lower take-up roll for receiving said lower feed sheet after said upper and lower feed sheets have advanced beyond said glove dispensing opening.

19. The glove donning and removal apparatus of claim 18, further comprising an upper and lower take-up roll drive and wherein said upper and lower take up rolls are driven at different speeds than said upper and lower feed sheets.

20. The glove donning and removal of claim 15, said grabber drive further comprising;
a first drive chain affixed to the base of a grabber on one side of said feed roll upper and lower feed sheets and a second drive chain affixed to the base of a grabber on the other side of said feed roll upper and lower feed sheets.

21. The glove donning and removal apparatus of claim 20, further comprising:
a cam follower affixed to the base of each of said grabbers and a first cam on said one side of said feed roll upper and lower feed sheets which engages the grabber driven by said first drive chain and a second cam on said other side of said feed roll upper and lower feed sheets which engages the grabber driven by said second drive chain.

22. The glove donning and removal apparatus of claim 15, further comprising:
a prime mover drivingly connected to said take-up reel for pulling said top and bottom feed sheets from their respective top and bottom feed rolls through said glove removal opening and winding said top and bottom feed sheets onto said take-up reel.

23. The glove donning and removal apparatus of claim 15, wherein said guides for said top feed sheet comprise a pair of side rolls that bias and guides said top feed sheet downwardly into engagement with the top surface of a user's gloved hand in said glove removal opening.

24. The glove donning and removal apparatus of claim 15, wherein said feed sheet drive comprises upper and lower feed sheet drive rollers which pull said upper and lower feed sheets from said feed roll.

25. The glove donning and removal apparatus of claim 24, further comprising a friction clutch connected to said feed roll to retard movement of said feed roll as said upper and lower feed sheets are pulled from said feed roll.

26. The glove donning and removal apparatus of claim 15, further comprising a prime mover having an output which drives said feed sheet drive and said grabber drive at a constant speed with respect to each other.

* * * * *